United States Patent [19]

Bruso

[11] Patent Number: 4,739,881
[45] Date of Patent: Apr. 26, 1988

[54] QUICK OPEN SYRINGE
[75] Inventor: Loran H. Bruso, Ontario, Calif.
[73] Assignee: Beckton, Dickinson and Company, Franklin Lakes, N.J.
[21] Appl. No.: 897,486
[22] Filed: Aug. 14, 1986
[51] Int. Cl.⁴ .............................................. B65D 85/38
[52] U.S. Cl. .................... 206/305; 206/569; 206/601; 206/603; 422/58; 422/61; 436/1
[58] Field of Search .............. 206/305, 363, 364, 365, 206/438, 439, 601, 603, 634, 569; 436/1; 422/61, 58

[56] References Cited

U.S. PATENT DOCUMENTS

| | | | |
|---|---|---|---|
| 3,036,700 | 5/1962 | Krug | 206/365 |
| 3,540,579 | 11/1970 | Hellstrom | 206/603 |
| 3,561,596 | 2/1971 | Knox | 206/365 |
| 4,150,744 | 4/1979 | Fennimore | 206/439 |
| 4,154,342 | 5/1979 | Wallace | 206/439 |
| 4,203,520 | 5/1980 | Schuster | 206/439 |
| 4,205,689 | 6/1980 | Brennan | 206/439 |
| 4,206,844 | 6/1980 | Thukamoto et al. | 206/439 |
| 4,266,667 | 5/1981 | Ishigaki | 206/634 |

Primary Examiner—David T. Fidei
Attorney, Agent, or Firm—Workman, Nydegger & Jensen

[57] ABSTRACT

A quick open syringe for use in testing an ethylene oxide sterilizer comprises a vented hollow container for receiving and holding a test unit therein. A lid with a handle covers an opening to the container and the container itself is formed with a piercing point. The quick open syringe and enclosed test unit can be positioned in a sterilizable peel pouch. After completion of a sterilization cycle, the container and lid handle may be grasped to remove the lid from the container and puncture the peel pouch with the point to enable removal of the test unit from the quick open syringe and the pouch.

17 Claims, 4 Drawing Sheets

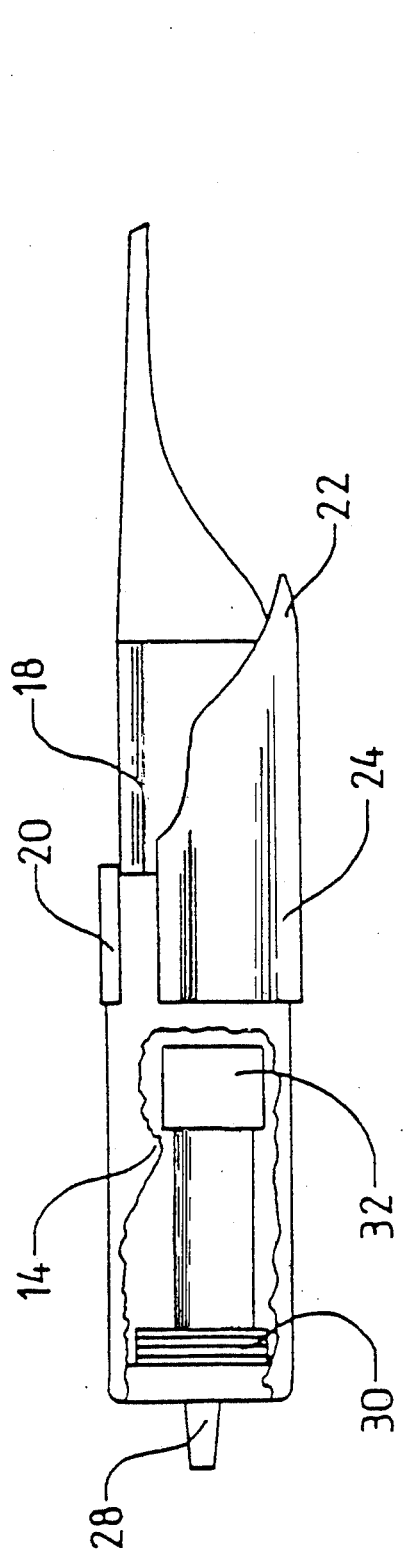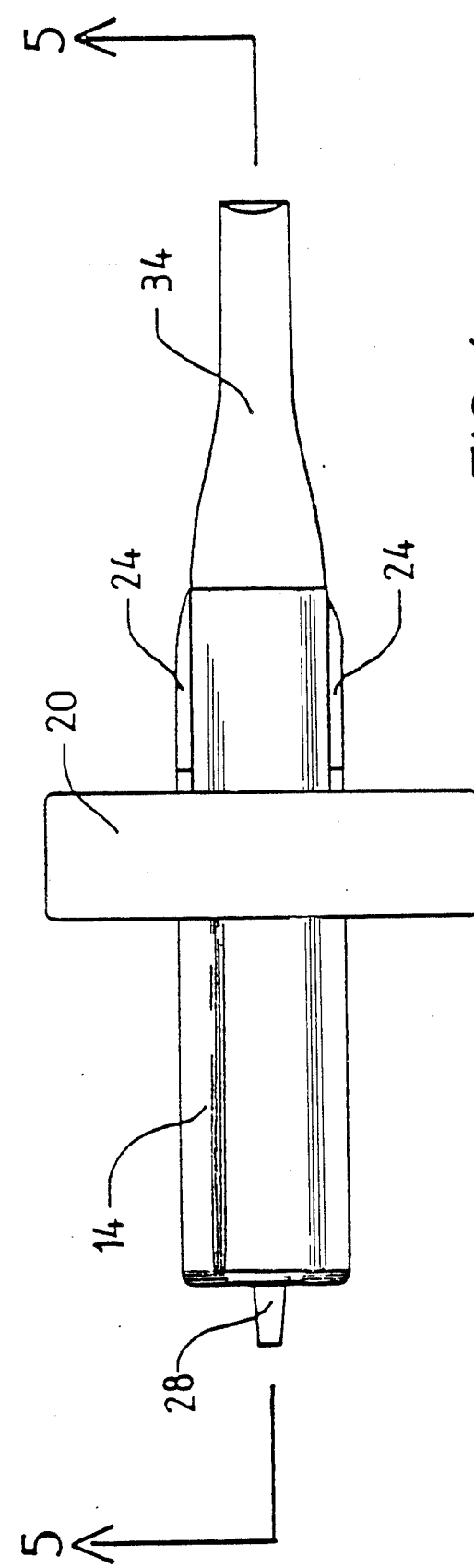

QUICK OPEN SYRINGE

BACKGROUND OF THE INVENTION

This invention relates generally to sterilizer test packs. Specifically, this invention relates to a pseudo syringe which can be loaded with a biological indicator and then placed in a pouch or envelope wherein it is subjected to a sterilization cycle. After completion of the sterilization cycle, the syringe of the present invention permits easy removal of the biological indicator from the syringe and the envelope. This invention is particularly, through not exclusively, useful in the testing of an Ethylene Oxide (EO) sterilizer.

DESCRIPTION OF THE PRIOR ART

It is well known in the medical profession that many medical procedures require devices and instruments which are thoroughly sterilized before being used for their intended purpose. Not all such devices and instruments, however, can be sterilized in the same manner. Consequently, several different sterilization procedures are followed. The particular procedure of interest here sterilizes devices and instruments through exposure to ethylene oxide gas.

For EO sterilization, as with any sterilization procedure, the operator must be certain that sterilizing conditions are achieved and that the instruments subjected to the sterilizing conditions are indeed sterile. For EO sterilization, specific procedural guidelines have been established and specially designed test packs have been suggested. Unfortunately, present procedures for using these test packs unnecessarily expose the operator to the toxic effects of ethylene oxide.

According to the Association for the Advancement of Medical Instrumentation (AAMI), an EO test pack should include a structure that simulates the items which are to be sterilized. Additionally, such a test pack should incorporate appropriate thermal and moisture barriers. With these considerations in mind, AAMI has recommended that an EO sterilizer test pack comprise a standard syringe into which a biological indicator has been placed. Further, AAMI recommends that the needle end of the syringe remain open and that the plunger be inserted into the syringe barrel in order to confine gas communication into the syringe through the opening at the needle end. The combination is then wrapped in a clean surgical towel and inserted into a peel pouch. The peel pouch and its contents are then subjected to an EO sterilization cycle. Subsequently, the biological indicator is examined to test the efficiency of the sterilization cycle.

For the purposes of the AAMI test, as well as for the present invention, any biological indicator well known in the art may be used. For example, any test pack having a biological spore strip innoculated with an appropriate population (1,000,000 generally) of spores from the Bacillus subtilis organism may be used. In any event, the object of any EO test pack is to make the contact of EO gas with the living spores contained in the biological indicator as challenging as possible. It will be appreciated by the skilled artisan that this challenge is accomplished by using the barrier effects of several factors. Firstly, the test pack should provide thermal insulation for the biological indicator. The object here, of course, is to challenge the EO sterilization system's heating ability. Secondly, the test pack should provide diffusion control to ensure adequate penetration of the EO gas into the devices being sterilized. This is accomplished by requiring the EO to traverse a torturous path before it contacts the biological indicator. Thirdly, the test pack should provide moisture control. Since moisture enhances the sterilization process, the removal of moisture from within the test pack provides a further challenge for the sterilizer. As is to be expected, all these controls must cooperate and be functional in order for there to be an efficacious test pack.

Once the sterilization cycle has been completed, the established procedure has been to remove the towel-wrapped syringe from the envelope, take the syringe out of the towel and disassemble the syringe. The biological indicator is then removed from the syringe and incubated to test the efficacy of the sterilization cycle. This procedure, however, has several disadvantages. Foremost, if the used test pack is opened shortly after the sterilization process is completed rather than being properly aerated at elevated temperatures for approximately 8-12 hours, the established procedure requiring removal and disassembly of the syringe can cause exposure of the operator to toxic EO gas for a significant amount of time. Ideally, however, the biological indicator should be removed from the test pack soon after sterilization without the unwanted exposure to EO gas. Secondly, since the test pack is assembled from standard hypodermic syringes, a substantial portion of a hospital's supply of syringes may be used for the testing of sterilization equipment instead of for their intended purposes. This is wasteful.

In light of the above, the present invention recognizes there is a need to duplicate the AAMI test procedure in a way that allows an early retrieval of the biological indicator while reducing operator exposure to the toxic affects of ethylene oxide gas. Further, the present invention recognizes a need for a test unit which will be relatively inexpensive and not require the destruction of syringes which could otherwise be used for their intended purposes.

Accordingly, it is an object of the present invention to provide a quick open syringe which can be disassembled while remaining in a sterilizable peel pouch envelope. It is another object of the present invention to provide a quick open syringe which can be manipulated to penetrate the peel pouch and create a hole in the sterilizable peel pouch through which the contents of the quick open syringe may be easily removed. It is yet another object of the present invention to provide an EO sterilizer test pack which will duplicate the accepted AAMI standards for EO sterilization. Still another object of the present invention is to provide a simulated syringe which obviates the need to destroy hypodermic syringes in a sterilizer test pack. Yet another object of the present invention is to provide a quick open syringe for testing the efficacy of an EO sterilization cycle which is easily manufactured, which is cost effective and which is easily used by the operator.

SUMMARY OF THE INVENTION

A preferred embodiment of the quick open syringe includes a vented hollow container into which a biological indicator test unit may be placed. The container has an opening which removably receives a lid that is formed with a handle. A position stabilizer is attached to the container to prevent rotation of the quick open syringe when it is placed within a sterilizable peel pouch envelope and a point is provided near the opening of the container which is suitable for piercing the envelope. While positioned inside the envelope, the handle of the lid and the container may be grasped and manipulated by the operator to pierce the envelope by the point. Thus, a hole in the envelope is made through which the test unit contents of the container may be easily removed.

The novel features of this invention, as well as the invention itself, both as to its structure and its operation will be best understood from the accompanying drawings taken in conjunction with the accompanying description in which similar reference characters refer to similar parts and in which:

BRIEF DESCRIPTION OF THE DRAWINGS

FIG. 3 is a side elevational view of the container and lid combination;

FIG. 4 is a top plan view of the container and lid combination;

DESCRIPTION OF THE PREFERRED EMBODIMENT

Figure 1:
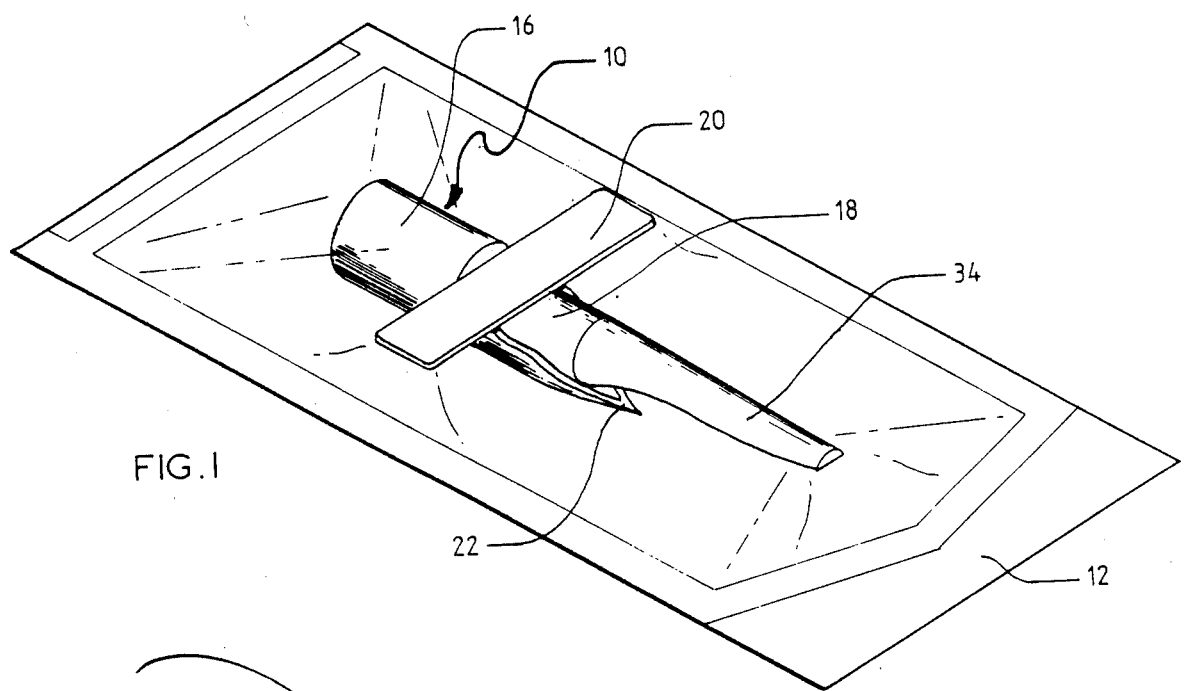
FIG. 1 is a perspective view of the quick open syringe placed within a peel pouch envelope.

Referring initially to FIG. 1, the quick open syringe of the present invention is shown generally designated 10. As seen in FIG. 1, the quick open syringe 10 is enclosed within a peel pouch envelope 12.

Figure 2:
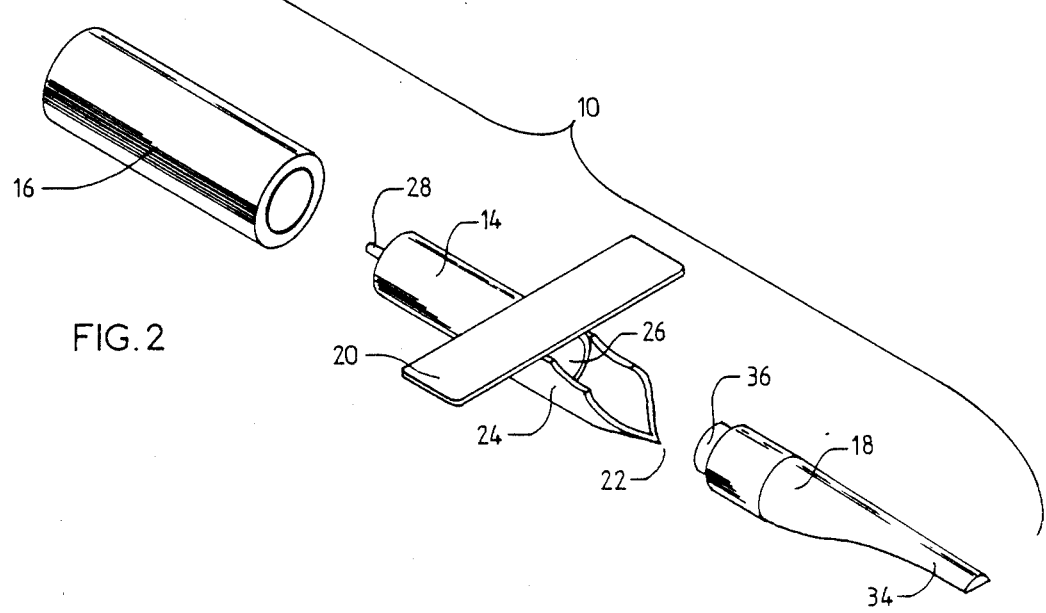
FIG. 2 is an exploded perspective view of the quick open syringe.

The major components of the quick open syringe 10 will be best appreciated by reference to FIG. 2 in which an exploded perspective view of syringe 10 shows these components to be a container 14, a thermal insulator 16 and a lid 18. Preferably, container 14 and lid 18 are made of polypropylene. Alternately, however, they may be made from any of several polymers, e.g., nylon, polycarbonate or polysulfone. Thermal insulator 16, on the other hand, is preferably made of a paper material such as cardboard. Insulator 16 may, however, be made of a material commonly referred to as CSR (central suppy room) wrap, foam plastic, cotton, sponge or cloth. Insulator 16 may also be formed as part of container 14 and still be within the intent of the present invention.

Figure 7:
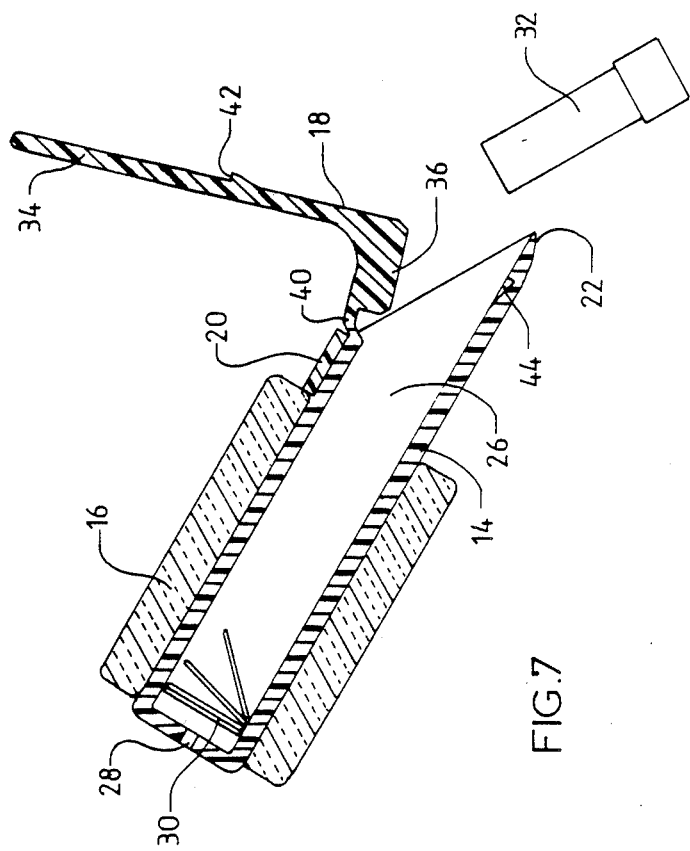
FIG. 7 is a cross-sectional side view of an alternate embodiment of the present invention.

FIG. 2 shows that container 14 is a hollow tubular structure which has a position stabilizer 20 fixedly attached thereto. Stabilizer 20 is generally oriented perpendicular to the longitudinal axis of container 14 to prevent rotation of syringe 10 when syringe 10 is placed within an envelope 12. Also seen on container 14 in FIG. 2 is a piercing point 22 that is formed on an adapter 24. Adapter 24 may be attached to container 14 by any manner well known in the art, such as by solvent bonding or may be molded as part of the container 14. Thus, it will be understood that point 22 may be formed directly on container 14 and may result by configuring container 14 as a truncated cylinder such as shown in FIG. 7.

Still referring to FIG. 2, it can be seen that container 14 has an opening 26 which provides access to the hollow interior of container 14. The end of container 14 opposite opening 26 is closed except for a vent 28 which is intended to simulate the open needle end required by the AAMI procedure. In order to regulate the diffusion control of syringe 10, vent 28 may be formed with varying apertures depending upon the particular needs and desires of the operator. Although vent 28, as shown in FIG. 2, is formed to represent the needle end of a standard syringe, it will be appreciated by the skilled artisan that vent 28 may be a simple hole as shown for the vent 28 in FIG. 7.

Lid 18 of quick open syringe 10 is shown in FIG. 2 with a handle 34 which is formed as an extension of the lid 18. Lid 18 also comprises a plug 36 which is adapted to be inserted and held in the opening 26 of container 14 by an interference fit. Preferably, when lid 18 is positioned in opening 26 of container 14, handle 34 will be diametrically opposite point 22 in their relationship with the longitudinal axis of container 14. This relationship is shown in FIGS. 1, 2, 3 and 5.

With lid 18 removed, a biological indicator 32 can be inserted into the container 14 through opening 26. Lid 18 can then be placed over opening 26 of container 14 to hold biological indicator 32 therein. As perhaps better seen in FIG. 5, the interior of container 14 should be of sufficient size to hold not only the biological indicator test unit 32 but also moisture control pads 30. The control pads 30 may be made of any moisture absorbing material such as blotter paper disks. The purpose of moisture control pads 30 is to remove moisture from the EO sterilizer testing to provide a dry and more challenging environment for the ethylene oxide to react with the test unit biological indicator 32.

Figure 5:
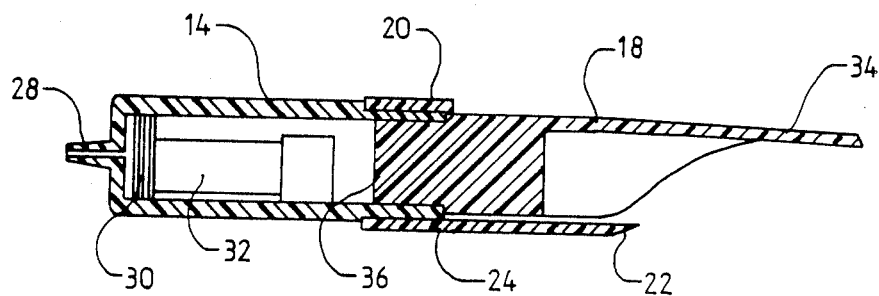
FIG. 5 is a side cross-sectional view of the container and lid of the present invention as seen along the line 5—5 in FIG. 4.

The assembly of container 14 with lid 18 is best seen with reference to FIGS. 3, 4 and 5. The entire assembly of syringe 10, however, is best seen in FIG. 1. There it will be seen that insulator 16 is positioned around container 14 to provide some degree of thermal protection for the contents of container 14. Various means, all well known in the pertinent art, may be used to position insulator 16 in surrounding association with the container 14. Preferably, as shown in FIG. 2, insulator 16 is formed as a tubular member which can slide over the outside portion of container 14.

An alternate embodiment of the present invention is shown in FIG. 7. In all essential aspects, the alternate embodiment functions in the same manner as the preferred embodiment. Also, with only slight modifications, the alternate embodiment is structurally similar to the preferred embodiment. Specifically, as seen in FIG. 7, a container 14 is configured as a truncated cylinder to form the point 22 which can be used to pierce the peel pouch envelope 12. Again, an insulator 16 is provided for surrounding relationship with the container 14 and a vent 28 is provided to allow access of ethylene oxide into the interior of the container 14. Unlike, the preferred embodiment, however, in the alternate embodiment the lid 18 is connected to container 14 by a hinge 40. It is understood that several types of hinges may be used for this purpose. Preferably, a living hinge 40 as shown in FIG. 7 is used. Further, the container 14 is formed with a recess 44 that cooperatingly engages with the latch 42 formed on handle 34 of the lid 18. It will be appreciated by the skilled artisan that this helps hold plug 36 over opening 26 for retaining contents within the container 14. Further, it will be appreciated that the handle 34 of lid 18 can be grasped and rotated to bring lid 18 into a position as shown in FIG. 7 and permit removal of contents, such as the test unit 32, from container 14. Like the preferred embodiment, the alternate embodiment contains a position stabilizer 20 located as shown in FIG. 7 to prevent rotation of the quick open syringe 10 within an envelope 12.

OPERATION

In its operation, the quick open syringe 10 of the present invention allows for the placement of a biological indicator test unit 32 inside a container 14. Also inside the container 14 are placed moisture control pads 30 for the purpose of absorbing moisture from the environment in which ethylene oxide is being used for sterilization. Once test unit 32 has been placed within container 14, lid 18 is placed over the opening 26 of container 14 for the purpose of holding the test unit 32 inside container 14. A thermal insulator 16 is placed in surrounding relationship to container 14 for the purpose of providing thermal insulation for the test pack 32 which is being held within the container 14. Also, a position stabilizer 20 is positioned on container 14 so that the entire combination when placed inside envelope 12 will not rotate.

Figure 6:
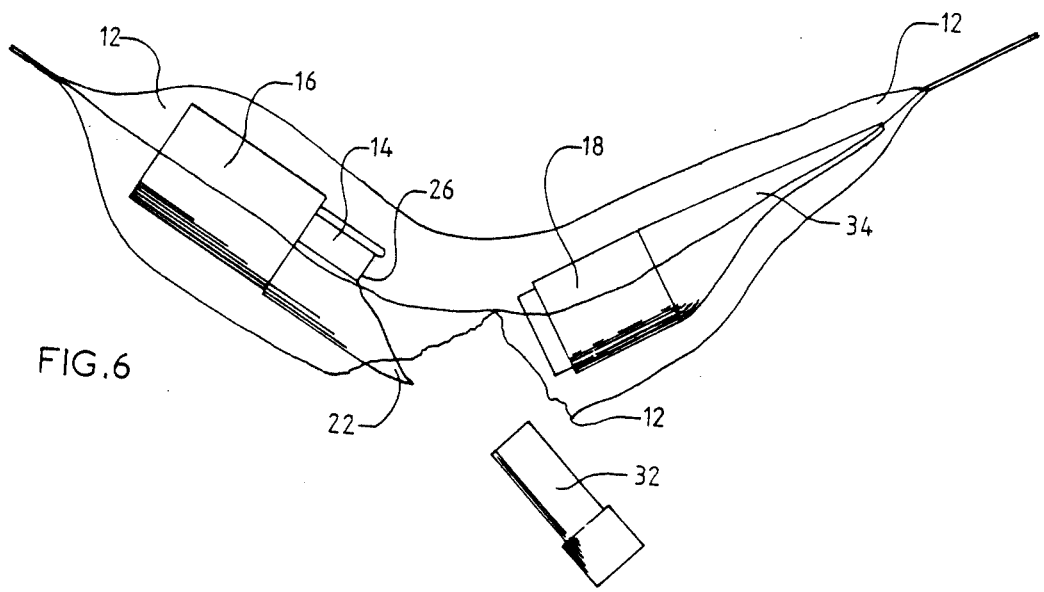
FIG. 6 is a side elevational view of the quick open syringe after being manipulated to open the peel pouch envelope for removal of the container's contents.

Once the quick open syringe 10 with its test unit 32 in place has been assembled, quick open syringe 10 is placed in a peel pouch envelope 12 and the entire combination is subjected to an ethylene oxide sterilization cycle. Upon completion of the sterilization cycle, the envelope 12 and the quick open syringe 10 contained therein are removed from the sterilizer, and the operator is able to grasp the thermal insulator 16 and container 14 in one hand and the handle 34 of lid 18 with the other hand. Referring now to FIG. 6, it will be appreciated that once the operator grasps the quick open syringe 10 in this manner, manipulation of the device in the directions of the arrows 38 will accomplish two purposes. Firstly, this manipulation of syringe 10 will separate the lid 18 from container 14. Secondly, it will allow point 22 to penetrate envelope 12 and create a hole in the envelope 12 through which the test unit 32 can be removed from the interior of container 14. Once test unit 32 has been removed from container 14, its contents may be incubated and later evaluated to determine the efficacy of the sterilization cycle.

While the particular quick open syringe as herein shown and disclosed in detail is fully capable of obtaining the objects and providing the advantages herein before stated, it is to be understood that it is merely illustrative of the presently preferred embodiment of the invention and that no limitations are intended to the details of construction or design herein shown other than as described in the appended claims.

I claim:

1. A quick opening apparatus for use with a test unit which comprises:
    a container for receiving said test unit therein, said container being formed with a vent and with an opening;
    a lid associated with said container for movement between a first position wherein said opening is covered by said lid and a second position wherein said opening is uncovered;
    an envelope to sealably hold said container therein; and
    a point formed on said container for piercing said envelope to expel said test unit from said container and from said envelope when said lid is moved from said first position to said second position.

2. An apparatus as cited in claim 1 further comprising a handle extending from said lid.

3. An apparatus as cited in claim 2 wherein said container is formed as a truncated cylinder having a first end and a second end with said second end canted transverse to the longitudinal axis of said cylinder to form said point.

4. An apparatus as cited in claim 3 further comprising a stabilizer attached to said container to prevent rotation of said container in said envelope.

5. An apparatus as cited in claim 4 further comprising an insulator mounted on a portion of said container to impede the transfer of heat to said container.

6. An apparatus as cited in claim 5 wherein said lid is hingedly attached to said container and said handle comprises means for holding said lid in said first position.

7. An apparatus as cited in claim 6 further comprising at least one pad placed within said container to absorb moisture entering said container.

8. An apparatus as cited in claim 7 wherein said test unit is sensitive to the presence of ethylene oxide gas for indicating exposure to the ethylene oxide gas.

9. An apparatus for releasing a device from an envelope which comprises:
    a container formed with an opening for receiving said device therein;
    a lid operatively associated with said container for movement between a first position wherein said opening is covered by said lid to hold said device within said container and a second position wherein said opening is uncovered; and
    means formed on said container for piercing said envelope to create a hole thereon for releasing said device from said container and said envelope when said lid is moved into said second position.

10. An apparatus as cited in claim 9 wherein said container is formed with a vent.

11. An apparatus as cited in claim 10 further comprising a handle extending from said lid.

12. An apparatus as cited in claim 11 further comprising a stabilizer attached to said container to prevent rotation of said container in said envelope.

13. An apparatus as cited in claim 12 further comprising an insulator mounted on a portion of said container to impede the transfer of heat to said container.

14. An apparatus as cited in claim 13 wherein said lid is hingedly attached to said container and said handle comprises means for holding said lid in said first position.

15. An apparatus as cited in claim 14 further comprising at least one pad placed within said container to absorb moisture entering said container.

16. An apparatus as cited in claim 15 wherein said test unit is sensitive to the presence of ethylene oxide gas for indicating exposure to the ethylene oxide gas.

17. A method for testing the efficiency of a sterilizer comprising the steps of:
    A. placing a test sensitive indicator into an apparatus comprising a container formed with an opening and a point and having a lid operatively associated with said container for movement between a first position wherein said opening is covered by said lid to hold said indicator within said container and a second position wherein said opening is uncovered to permit removal of said indicator from said container;

B. placing the combination of said indicator and said container into an envelope;

C. subjecting said envelope and its contents to a sterilization cycle;

D. moving said lid into said second position to uncover said opening and pierce said envelope with said point for removing said indicator therefrom; and E. observing said indicator to determine the efficiency of the sterilizer.

* * * * *